United States Patent [19]

Kawabe et al.

[11] Patent Number: 4,757,021
[45] Date of Patent: Jul. 12, 1988

[54] RECOMBINANT PLASMID AND MICROBIAL STRAIN TRANSFORMED BY SAID PLASMID

[75] Inventors: Haruhide Kawabe; Kazumoto Hirabayashi; Hazime Horii; Hirofumi Arimura, all of Osaka; Masayuki Nishida; Tadakazu Suyama, both of Kyoto, all of Japan

[73] Assignee: Green Cross Corporation, Osaka, Japan

[21] Appl. No.: 795,144

[22] Filed: Nov. 5, 1985

[30] Foreign Application Priority Data

Nov. 5, 1984 [JP] Japan ................... 59-232683

[51] Int. Cl.⁴ .............. C12N 1/18; C12N 15/00; C12N 1/00
[52] U.S. Cl. ............... 435/256; 435/172.3; 435/320; 935/28; 935/37
[58] Field of Search ............... 435/317, 172.3, 256, 435/320; 935/28, 37, 69

[56] References Cited

U.S. PATENT DOCUMENTS 4,615,974  10/1986  Kingsmen et al. ............ 435/68

FOREIGN PATENT DOCUMENTS 0105149  11/1984  European Pat. Off. .

OTHER PUBLICATIONS

Broach, Methods In Enzymology, vol. 101, Part C, pp. 307–324 (1983).
Jayaram et al., Cell vol. 34, pp. 95–104, Aug. 1983.
Valenzuela et al., Nature, vol. 298, pp. 347–350, Jul. 22, 1982.
Chemical Abstracts, vol. 102, 40750 a, 1985.

*Primary Examiner*—Alvin E. Tanenholtz
*Attorney, Agent, or Firm*—Sughrue, Mion, Zinn, Macpeak, and Seas

[57] ABSTRACT

A recombinant plasmid wherein at least two DNA fragments containing a Baker gene and a Charlie gene of the yeast 2 μm circular plasmid are incorporated into a plasmid containing genes encoding a physiologically active substance is disclosed. Also, a strain transformed by the recombinant plasmid is disclosed.

8 Claims, 1 Drawing Sheet

Figure
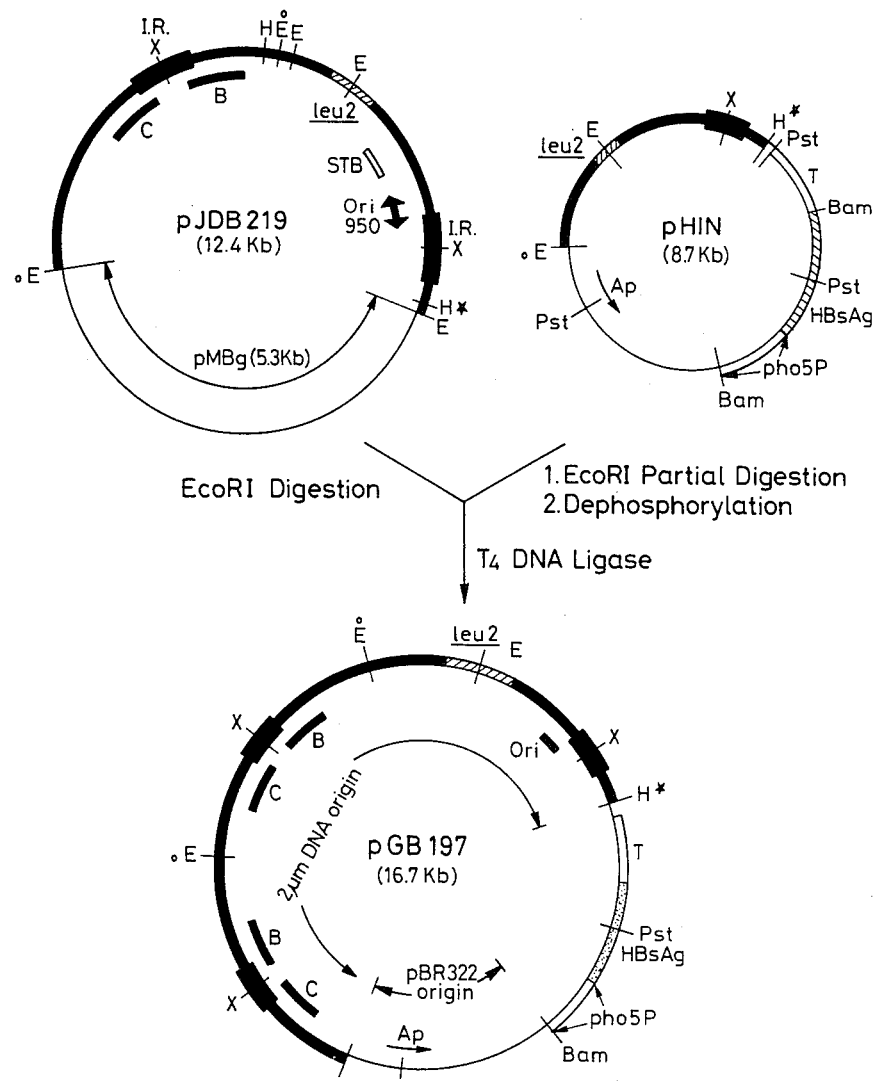

RECOMBINANT PLASMID AND MICROBIAL STRAIN TRANSFORMED BY SAID PLASMID

The present invention relates to a recombinant plasmid and a microbial strain transformed by said plasmid. More particularly, the invention relates to a recombinant plasmid capable of efficiently expressing heterologous genes encoding a physiologically active substance, as well as a microbial strain transformed by said plasmid. The present invention will prove very useful in the field of producing physiologically active substances by genetic engineering.

The well known yeast strain, *Saccharomyces cerevisiae*, contains a cryptic plasmid (2 μm circular) with 6,318 base pairs. The complete nucleotide base sequence of this plasmid has already been determined (Hartley anad Donelson; *Nature*, 286: 860 (1980)). Yeast containing this cryptic plasmid is referred to as a Cir+ strain and yeast lacking this plasmid is referred to as a Cir° strain.

The cryptic plasmid (2 μm circular) has a copy number of 50 to 100 and is potentially a vector having a relatively high transcipriton efficiency. This plasmid is known to contain at least 4 genes. It has been reported that the products (Rep 1 and Rep 2) of a Baker gene (hereinafter "B gene") and a Charlie gene (hereinafter "C gene"), both being encoded by the plasmid, help it replicate so as to increase its copy number and, hence, its stability (Broach et al; *Cell*, 28: 203 (1982) and ibid, 34: 95, (1983)). It has also been reported that in order to maintain the 2 μm circular plasmid stably within bacterial cells, an STB gene involved in stable distribution is necessary in addition to Rep 1 and Rep 2 (Kikuchi; *Saibo*, 15: 131 (1983)). According to another report, pCV20 and pCV21, which contain the entire portion of the 2 μm circular plasmid, are two plasmids having high copy numbers in a Cir° strain lacking the Rep gene product (Broach et al; *Enzymology*, 101: 307-325 (1983)).

SUMMARY OF THE INVENTION

The primary object, therefore, of the present invention is to provide a recombinant plasmid capable of efficiently expressing heterologous genes encoding a physiologically active substance by means of using genes of the above described 2 μm circular plasmid.

Another object of the present invention is to provide a microbial strain transformed by such recombinant plasmid.

The first object of the invention is achieved by a recombinant plasmid constructed by incorporating at least two DNA fragments containing the B gene and C gene of the yeast 2 μm circular plasmid into a plasmid containing genes encoding a physiologically active substance. The second object has been attained by a microbial strain transformed by such a recombinant plasmid.

BRIEF DESCRIPTION OF THE DRAWINGS

The FIGURE is a flowsheet illustrating how pJDB 219 (12.4 kb) is linked to pHIN (8.7 kb), wherein E, X, Pst, Bam and H respectively represent cleavage sites of EcoRI, XbaI, PstI, BamHI and HindIII, with IR representing an inverted repeat, leu 2 being a 2-isopropylmalate dehydrogenase gene, B being a Baker gene, C being a Charlie gene, Pho 5 being a repressible acid phosphatase gene, P being a promoter, HBsAg being a hepatitis virus surface antigen gene, Ori being a replication initiation point, Ap being an ampicillin-resistant gene, and T being a terminator.

DETAILED DESCRIPTION OF THE INVENTION

The various aspects of the present invention are hereunder described in detail.

(a) Preparation of the yeast 2 μm circular plasmid:

The yeast plasmid (2 μm circular) is prepared in accordance with the method of Hartley et al. (*Nature*, 286: 860 (1980)). Plasmids containing B and C genes derived from this 2 μm plasmid include pJDB219, pJDB207, pCV20, and pCV21. pJDB219 and pJDB 207 are readily available.

(b) Preparation of DNA fragments containing B and C genes:

The plasmid obtained in (a) containing B and C genes is cleaved by restriction enzymes to separate and recover fragments containing the B and C genes. The cleavage is performed by digestion with appropriate restriction enzymes for obtaining DNA fragments containing at least B and C genes. There is no particular limitation on the restriction enzymes that can be used for this purpose, and suitable restriction enzymes may be used either individually or in combination for obtaining the desired fragments. An illustrative suitable restriction enzyme is EcoRI. When employing this enzyme the DNA fragment may contain an STB gene and/or Ori gene in addition to the B and C genes. The digestion scheme will proceed as follows: an aqueous solution containing a starting plasmid containing B and C genes is adjusted to the conditions appropriate for the respective restriction enzymes used (see Table 1 below), and after adding these enzymes in suitable amounts, treatment is conducted for 1 to 2 hours. The desired DNA fragments may be recovered by electrophoresis using, for example, the procedure of Robert et al. (*Methods in Enzymology*, 68: 176-182 (1979)). A DNA fragment of about 4 kilobases may be obtained by digestion with EcoRI. The existence of B and C genes in the resulting DNA fragments can be verified by checking the length of the DNA fragments obtained by digestion with specific restriction enzymes (see The Molecular Biology of the Yeast Saccharomyces, "Life Cycle and Inheritance", 445-470 (1982)).

TABLE 1

| Restriction enzyme | Tris buffer (mM) | pH | NaCl (mM) | MgCl$_2$ (mM) | (NH$_4$)$_2$SO$_4$ (mM) | KCl (mM) | Mercaptoethanol |
|---|---|---|---|---|---|---|---|
| Acc I | 10 | 7.5 | 60 | 7 | — | — | 5 |
| Alu I | 6 | 7.6 | 50 | 6 | | | 5 |
| Ava II | 6 | 8.0 | 60 | 10 | | | 5 |
| BamH I | 10 | 8.0 | 100 | 7 | | | 5 |
| Bcl I | 6 | 7.4 | | 10 | | 75 | — |
| Bgl I | 10 | 7.4 | 66 | 10 | | | 2 |
| Bgl II | 10 | 7.5 | 100 | 10 | | | 5 |
| BstE II | 6 | 7.9 | 150 | 6 | | | — |
| Cla I | 6 | 7.9 | 50 | 6 | | | 5 |
| EcoR I | 100 | 7.5 | 50 | 7 | — | — | 5 |
| Fna4H I | 6 | 7.4 | 6 | 6 | | 5 | 5 |
| Hae III | 10 | 7.5 | 60 | 7 | | | 5 |
| Hinc II | 10 | 8.0 | 60 | 7 | | | 5 |
| Hind III | 10 | 7.5 | 60 | 7 | | | 5 |
| Kpn I | 6 | 7.5 | 6 | 6 | | | — |
| Pst I | 20 | 7.5 | — | 10 | 50 | — | — |
| Pvu II | 6 | 7.5 | 60 | 6 | | | — |
| Rsa I | 6 | 8.0 | 50 | 12 | | | 5 |
| Sau 96 I | 6 | 7.4 | 60 | 15 | | | 5 |
| Sma I | 6 | 8.0 | | 6 | | 20 | 5 |

TABLE 1-continued

| Restriction enzyme | Tris buffer (mM) | pH | NaCl (mM) | MgCl₂ (mM) | (NH4)2SO4 (mM) | KCl (mM) | Mercaptoethanol |
|---|---|---|---|---|---|---|---|
| Xba I | 6 | 7.9 | 50 | 6 | | | |

(c) Preparation of plasmid containing genes encoding a physiologically active substance:

A broad range of known physiologically active substances are contemplated by the present invention and they include, but are not limited to, interferons, plasminogen activators and HBsAg. A particularly preferred example is HBsAg. A preferred plasmid containing genes encoding a physiologically active substance is such that it already contains a 2 µm plasmid derived system for controlling the expression of the particular physiologically active substance, such as Ori, promoter, operator or terminator. It is particularly preferred that a restriction enzyme site suitable for obtaining DNA fragments containing B and C genes is present in portions of the plasmid other than said expression controlling gene. In the absence of any suitable restriction enzyme site, methods such as the addition of dC tails and dG tails, the use of linkers and the joining of flush ends by SI nuclease may be employed.

An advantageous plasmid is the one that was developed by Biogen, S.A. and which contains genes coding for a physiologically active substance (see Unexamined Published Japanese Patent Application No. 48082/1984 and British Pat. No. 2125047: p31R/IF(α-2), pJDB207/PHO5/HBVs 14 (hereinafter "pHIN")).

(d) Linking B and C DNA fragments to plasmid containing genes encoding a physiologically active substance:

In accordance with the routine procedure (Cohen, S.N. et al., Proceedings of the National Academy of Science of the U.S.A., 69: 2110 (1972)), the DNA fragments of B and C genes are joined to the restriction enzyme cleaved sites of the plasmid of interest by T4DNA ligase, so as to construct a recombinant plasmid. Two or more DNA fragments are linked to the physiologically active substance encoding genes in the same direction as illustrated in the FIGURE.

(e) Preparation of host

The B and C genes used in the present invention are derived from the yeast 2 µm circular plasmid, so a yeast strain. A particularly preferred host is the 2 µm plasmid deficient yeast strain Cir°, and a specific example is pho80 Cir° strain derived from GRF18 pho80 (Biogen, S.A.) which is a derivative of known microorganism GRF18 (Biogen, S.A.). For the methods of separating and verifying this yeast strain, see Reference Example 1.

(f) Transformation

Host transformation by the recombinant plasmid of the present invention may be performed by a known procedure (Hinnen et al., Proceedings of the National Academy of Science of the U.S.A., 75: 1929 (1978)).

(g) Cultivation of transformant

The transformant obtained in step (f) is cultured in a known medium suitable for the specific host used. An advantageous medium is YNB liquid medium (0.7% yeast nitrogen base (Difco), 2% glucose and 2% agar). The cultivation is usually performed at 15°–32° C. for 20–50 hours, optionally accompanied by aeration or agitation as required. After the cultivation, the microbial cells are collected by a known method, for example, centrifugation. The collected cells are suspended in a suitable buffer solution, and following optional ultrasonication, the supernatant is recovered by centrifugation. The desired physiologically active substance has been produced within the recovered supernatant and may be purified by an appropriate procedure such as an immobilized column using a monoclonal antibody or affinity chromatography using a hydrophobic group.

The plasmid thus constructed by the present invention enables a desired physiologically active substance to be produced in much higher quantities than plasmids lacking B and C genes and the conventional replication system using the yeast Cir+ as a host.

REFERENCE EXAMPLE 1

Separation of the yeast Cir° strain:

The yeast Cir° strain was separated as an advantageous host to be transformed.

Plasmid pJDB219-Tn was prepared by inserting a transposon (Tn) 903 DNA fragment (1.8 kb) containing an aminoglycoside 3'-phosphotransferase gene into a SalI site on pJDB 219 (see above) containing the 2 µm plasmid derived B and C genes. The transposon was taken out from pHING-2 (Biogen, S.A.) in the conventional manner. A yeast GRF18 Cir+ strain (GB 2125047) was transformed by the thus-prepared plasmid. The yeast strain was obtained from Biogen, S.A. The transformant was shake-cultured in YPD liquid medium 1% (yeast extract, 2% polypeptone and 2% glucose) at 37° C. for 4 days. The cultured solution was ultrasonicated with an ultrasonic vibrator (Tomy Seiko, 20 W). After confirming microscopically that any clumps of microbial cells were dispersed, the ultrasonicated solution was spread on YPD agar plate (YPD liquid medium+2% agar) so that single colonies would form and cultured at 30° C. for 2 days. With the YPD agar plate used as the master plate, the colonies were replicated onto G418 (YPD agar plate containing 500 γ/ml of 2-deoxystreptamin) to pick up G418-sensitive strains. In this manner, 230 strains lacking the pJDB 219-Tn plasmid were obtained. These 230 pJDB 219-Tn deficient strains were checked for the presence of the 2 µm plasmid DNA by the procedure of Cameron et al. (*Nucleic Acids Research*, 4: 1429. (1977)). More specifically, the strains were inoculated on a YPD agar plate and cultured at 30° C. for 1 to 2 days. Culture cells obtained by touching the colony with a platinum loop were suspended in 0.6 ml of a buffer solution (50 mM phosphate buffer (pH 7.5) - 1.2M sorbitol—20 mM 2-mercaptoethanol—500 mcg/ml Zymolyase) in a conical tube (1.5 ml). Following incubation at 30° C. for 90 minutes, 30 µl each of the solutions of 1M EDTA (pH, 8.0), 2M tris buffer and 10% SDS, as well as 2 µl of diethyl pyrocarbonate were added to the culture solution and mixed well, followed by incubation at 65° C. for an additional 40 minutes.

The culture solution was left on an ice bath for 10 minutes, mixed with 160 µl of 5M potassium acetate and further left to stand on an ice bath for 60 minutes or more. The solution was then subjected to centrifugation for 5 minutes with a desktop centrifuge (Eppendorf 5414) and the supernatant was transferred into a sterile conical tube. After adding an equal volume of ethanol, the mixture was left to stand at room temperature for 10 minutes and centrifuged for 10 minutes. The resulting precipitate was dried and dissolved in 40 ml of TE solution (10 mM tris-HCl (pH, 7.5) and 1 mM EDTA).

To the solution, RNase A (Worthington Biochemicals, Inc.) was added to give a final concentration of 10 mcg/ml, followed by 30-min incubation at 37° C. to make a DNA sample. The entire portion of this DNA sample was subjected to electrophoresis through 1% agarose gel so as to check for the presence of the 2 μm plasmid in the sample. Of the 230 G418-sensitive strains (pJDB219-Tn deficient strains) tested by this procedure, 70 strains were found to lack 2 μm DNA bands. Of these 70 strains, 17 strains were selected in view of their growth state and properties and cultured in 10 ml YPD liquid medium by procedures which were essentially the same as described above. By 1% agarose gel electrophoresis, it was verified that the cultures contained neither pJDB219-Tn nor 2 μm DNA fragments In this manner, yeast strain Cir° was prepared.

Further verification by the Southern hydridization technique (see above) revealed that the 17 strains obtained above lacked pJDB219-Tn prepared by labelling an EcoRI cleaved DNA fragment (4 kb) of pJDB219 by the nick translation technique. This proble had a specific activity of $1 \times 10^8$ c.p.m./DNA μg.

EXAMPLE 1

(1) Preparation of B and C gene DNA fragments:

In a solution comprising 100 mM tris—HCl (pH 7.5), 7 mM $MgCl_2$, 50 mM NaCl and 7 mM 2-mecraptoethanol was mixed 3 μg of pJDB219 (see above) and 5 U of EcoRI (Takara Shuzo Co., Ltd.). The mixture was held at 37° C. for 1 hour to ensure complete digestion. The reaction solution was subjected to electrophoresis through a 1% agarose slab gel in a buffer solution (40 mM Trisma Base$^R$, 20 mM sodium acetate, 1 mM EDTA, pH adjusted to 8.3 with acetic acid) at 75 volts for 4 hours. The agarose gel was stained with an ethidium bromide solution (0.5 mcg/ml) and a slice of agarose gel containing the desired DNA fragment (4 kb) was cut out using a UV light. The DNA bands of interest were isolated from the gel by electrophoresis (Robert et al., Methods in Enzymology, 68: 176 (1979)).
(2) Preparation of plasmid containing genes encoding a physiologically active substance Plasmid pHIN (8.7 kb) (see above) was digested with EcoRI using a reaction solution of the same composition as used in step (1). This solution was mixed with 3 μg of pHIN DNA and 1 U of EcoRI (Takara Shuzo Co., Ltd.) and the mixture was subjected to reaction at 37° C. for 15 minutes. The reaction solution was subjected to electrophoresis through a 0.8% low-melting-point agarose (Bio-Rad Laboratories, Inc.) as in step (1).

An agarose slice containing a pHIN (8.7 kb) DNA band having only one EcoRI cleavage site was cut out, dissolved in an equal volume of TE buffer solution at 65° C., treated with phenol, and mixed with 2 volumes of ethanol to precipitate pHIN DNA. The resulting DNA was treated with 1 U of alkali phosphatase (Boehringer & Mannheim) in a buffer solution (50 mM tris-HCl and 0.1 mM EDTA with pH 8.0) at 37° C. for 30 minutes, so as to remove 5'-terminal phosphoric acid. Following phenol treatment, the solution was mixed with ethanol to precipitate DNA.
(3) Gene recombinant procedure The two DNA fragments obtained in step (2) were treated with 5 units of $T_4$DNA ligase in a buffer solution (66 mM tris-HCl with pH 7.6, 6.6 mM $MgCl_2$, 10 mM DTT and 1 mM ATP) overnight at 16° C. Escherichia coli was transformed with the reaction product and the transformant was inoculated on L agar (1% polypeptone, 0.5% yeast extract, 1% NaCl and 1.5% agar) containing 20 γ/ml of ampicillin, followed by cultivation overnight at 37° C. Among the resulting ampicillin-resistant colonies, strains of E. coli having a pHIN plasmid incorporating the B and C genes were freed of the plasmid by the alkaline extraction procedure (Birnboim, H. C. and Doly, J., Nucleic Acids Research, 7: 1513 (1979)) and patterns of digestion by restriction enzymes were checked. By these procedures, HBsAg expressing plasmid pGB 197 (about 16.7 kb) containing B and C genes was constructed. This plasmid did not contain the 4 kb fragment of rJDB219 at the leu 2 EcoRI site of pHIN, and two B and C gene fragments were present in the pHIN as they were linked together in the same direction.
(4) Transformation GRF 18 pho Cir° strain obtained in Reference Example 1 was transformed on a leucine-free YNB plate by the method of Hinnen et al (see above) using the plasmid obtained in step (3). By this procedure, pGB 197/GRF 18 pho 80 Cir° strain was obtained. This strain, named Saccharomyces cerevisiae YGC 1, has been deposited at Fermentation Research Institute, Agency of Industrial Science and Technology, 1-3, Higashi 1 chome, Yatabe-machi, Tsukuba-gun, Ibaraki, Japan under accession number FERM BP-931.
(5) Production of HBsAg A YNB liquid medium (1,000 ml) was inoculated with pGB 197/GRF 18 pho 80 Cir° and subjected to shake culture at 30° C. for 1 day. The culture solution was treated as in Example 2 to obtain an HBsAg-containing supernatant.

EXAMPLE 2

In order to confirm the advantages of the present invention, an experiment was conducted comparing a known plasmid and the recombinant plasmid of the present invention with respect to their ability to produce a physiologically active substance, i.e., HBsAg. The samples used were the Saccharomyces cerevisiae strain GRF18 pho80 Cir°, transformed by the recombinant plasmid pGB197 of Example 1 and a control yeast strain, Saccharomyces cerevisiae GRF18 pho80 Cir+, transformed by pHIN (GB2125047 of Biogen, S.A.).

Each of the strains was shake-cultured in YNB liquid medium (see above) at 30° C. for 2 days (O.D.$_{540}$ 1.3). The culture solution was centrifuged to collect the cultured cells, which were washed with a buffer solution (50 mM tris-HCl (pH, 7.5), 1 mM EDTA and 1 mM PMSF (phenyl-methyl-sulfony-fluorite)), suspended in an equal volume of the same buffer solution, and ultrasonicated for 9 minutes with an ultrasonic vibrator (Tomy Seiko, 200 W). The resulting solution was centrifuged at 10,000×g for 20 minutes and the supernatant was recovered. The activities of HBsAg in the supernatants thus recovered were determined with An Antihebcell (RPHA reagent of Green Cross Corporation), and the results are shown in Table 2 below.

TABLE 2

| Plasmid | | HBsAg Activity |
|---|---|---|
| pHIN | Saccharomyces cerevisiae GRF18 pho80 Cir+ | 1:1,024 |
| pGB197 | Saccharomyces cerevisiae GRF18 pho80 Cir° | 1:8,192 |

The above data demonstrate that the recombinant plasmid of the present invention has the ability to produce HBsAg in a quantity approximately 8 times as great as that produced by the conventional plasmid. The two plasmids were found to have the same copy number as determined by the Southern hybridization technique of Rigby et al. (Journal of Molecular Biology, 113: 237 (1977)).

While the invention has been described in detail and with reference to specific embodiments thereof, it will be apparent to one skilled in the art that various changes and modifications can be made therein without departing from the spirit and scope thereof.

What is claimed is:

1. A recombinant plasmid wherein at least two DNA fragments each containing a Baker gene and a Charlie gene of the yeast 2 μm circular plasmid are incorporated into a plasmid containing genes encoding a physiologically active substance.

2. The recombinant plasmid according to claim 1, wherein two of said DNA fragments are linked in the same direction.

3. The recombinant plasmid according to claims 1 or 2, wherein said physiologically active substance is HBsAg.

4. The recombinant plasma according to claim 1, wherein said plasmid also contains a 2 μm plasmid derived system for controlling the expression of said physiologically active substance.

5. A yeast strain transformed by a recombinant plasmid wherein at least two DNA fragments each containing a Baker gene and a Charlie gene of the yeast 2 μm circular plasmid are incorporated into a plasmid containing genes encoding a physiologically active substance.

6. The transformed strain according to claim 4, wherein two of said DNA fragments are linked in the same direction.

7. The transformed strain according to claims 4, 5 or 6, wherein said physiologically active substance is HBsAg.

8. The transformed yeast strain according to claim 5, wherein said plasmid also contains a 2 μm plasmid derived system for controlling the expression of said physiologically active substance.

* * * * *